United States Patent
Van Dyke

(10) Patent No.: US 11,918,446 B2
(45) Date of Patent: Mar. 5, 2024

(54) FLATULENCE SILENCER AND ODOR ELIMINATOR

(71) Applicant: Richard L. Van Dyke, Sherman, IL (US)

(72) Inventor: Richard L. Van Dyke, Sherman, IL (US)

(73) Assignee: Richard L. Van Dyke, Sherman, IL (US)

( * ) Notice: Subject to any disclaimer, the term of this patent is extended or adjusted under 35 U.S.C. 154(b) by 251 days.

(21) Appl. No.: 17/514,662

(22) Filed: Oct. 29, 2021

(65) Prior Publication Data
US 2022/0133556 A1    May 5, 2022

Related U.S. Application Data

(60) Provisional application No. 63/109,449, filed on Nov. 4, 2020.

(51) Int. Cl.
*A61F 13/84* (2006.01)
*A61F 13/15* (2006.01)
*A61F 13/51* (2006.01)

(52) U.S. Cl.
CPC .... *A61F 13/84* (2013.01); *A61F 2013/15138* (2013.01); *A61F 2013/15878* (2013.01); *A61F 2013/1591* (2013.01); *A61F 2013/5109* (2013.01); *A61F 2013/842* (2013.01); *A61F 2013/8455* (2013.01)

(58) Field of Classification Search
CPC .............. A61F 13/2011; A61F 13/8405; A61F 2013/1513; A61F 2013/15138; A61F 2013/5109; A61F 2013/8408; A61F 2013/842; A61F 2013/8423; A61F 2013/8455

See application file for complete search history.

(56) References Cited

U.S. PATENT DOCUMENTS

| | | | |
|---|---|---|---|
| 2,742,042 A * | 4/1956 | Flanders | ................. A61F 13/15 604/377 |
| 4,182,335 A | 1/1980 | Matrullo | |
| 4,880,417 A | 11/1989 | Yabrov et al. | |

(Continued)

FOREIGN PATENT DOCUMENTS

| | | |
|---|---|---|
| KR | 101008171 B1 | 1/2011 |
| WO | WO9826808 A2 | 6/1998 |
| WO | WO2019158672 A1 | 8/2019 |

OTHER PUBLICATIONS

Discreetz Fart Eliminator Solutions!, "Fart odor eliminator—quick start explainer video—flatulence odor control products & fart silencer!", Aug. 19, 2020 (Aug. 19, 2020) [online] retrieved from <URL: https://www.youtube.com/watch?v=0MqRMSFy9RA>.

(Continued)

*Primary Examiner* — Catharine L Anderson
(74) *Attorney, Agent, or Firm* — IP & T GROUP LLP

(57) ABSTRACT

The invention relates generally to device and methods for controlling flatulence release. In particular, the device and method of the present invention is effective for suppressing, reducing, or eliminating noise and odor of flatus gas at the anal opening. The device contains an odor absorbing material and is configured to be inserted into or pressed against the anal opening.

14 Claims, 5 Drawing Sheets

(56) References Cited

U.S. PATENT DOCUMENTS

| | | | |
|---|---|---|---|
| 5,665,081 A | 9/1997 | Grosse | |
| 5,695,484 A * | 12/1997 | Cox | A61F 2/0009 |
| | | | 604/304 |
| 6,221,004 B1 | 4/2001 | Kahl | |
| 6,313,371 B1 | 11/2001 | Conant et al. | |
| 8,062,277 B2 * | 11/2011 | Fleming | A61F 13/47209 |
| | | | 604/385.18 |
| 8,353,884 B2 | 1/2013 | Hansen et al. | |
| 2003/0187412 A1 * | 10/2003 | Martin | A61F 13/8405 |
| | | | 604/359 |
| 2007/0093738 A1 * | 4/2007 | Krecker | A61F 13/14 |
| | | | 602/61 |
| 2009/0093784 A1 | 4/2009 | Hansen et al. | |
| 2009/0247972 A1 | 10/2009 | Fleming | |

OTHER PUBLICATIONS

International Search Report & Written Opinion from corresponding application PCT/US21/57347 dated Jan. 27, 2022 (8 pages).

\* cited by examiner

FLATULENCE SILENCER AND ODOR ELIMINATOR

CROSS-REFERENCE TO RELATED APPLICATIONS AND CLAIM TO PRIORITY

This application is related to and claims the priority of U.S. Provisional Patent Application No. 63/109,449, filed Nov. 4, 2020, which is incorporated herein by reference.

FIELD OF THE INVENTION

The invention relates generally to device and methods for controlling flatulence release. In particular, the device and method of the present invention is effective for suppressing, reducing, or eliminating noise and odor of flatus gas at the anal opening.

BACKGROUND OF THE INVENTION

Flatulence, fart, passing gas, passing wind, all describe the emission of gas from the intestine through the anus, which when occurring in public can be very embarrassing and cause one to feel uncomfortable around others. Sometimes, when the gas escapes rapidly from the anus, a loud noise can result due to reverberations of the tissues of anus. The emitted gas comprises mostly of methane and sulfur-containing gas, such as hydrogen sulfide. The odor's severity depends on the composition of the flatus gas which varies hour to hour and person to person. There have been various attempts to solve or moderate flatulence; however, none has answered the need in such a way as to become an acceptable and effective solution commonly used in everyday life.

Some examples of current methods do not effectively solve the two most embarrassing aspects of flatulence, noise, and foul odor. The offensive noise is caused by gas passing in sufficient quantities and velocities forcing the opening of the anus and/or the buttocks to flap, slap, and reverberate loudly.

U.S. Pat. No. 4,182,335 discloses an anal filter, but that filter does not control or stop the flapping noise of the anus from flatus. That filter is also bulky and does not effectively eliminate offensive odors.

U.S. Pat. No. 6,313,371 discloses a wearable and regenerative flatus and genitalia odor removal apparatus which is taped to undergarments and offers no effective remedy for the loud noises made by one's uncontrolled slapping anus or buttocks. The apparatus is also placed too far from the anus (the source) making it less effective for odor control.

U.S. Pat. No. 5,665,081 discloses an absorbing anal pad which is bulky, complex, uncomfortable. The pad is essentially a feminine napkin filled with granulated charcoal chambers. But the pad is ineffective in preventing the noises made by the gas escaping loudly from a reverberating anus or the buttocks.

U.S. Pat. No. 8,353,884 discloses an anal patch designed for incontinence. The patch is a complex device, using messy adhesives and cannot be tucked/inserted into the anal opening when desired to further control the anus and buttocks from flapping together making flatus gas noises.

The prior devices and methods offer little or nothing to substantially reduce or eliminate flatus noise. Additionally, concerning odor removal, the prior devices are placed too far away from the anal opening, allowing some of the gas to inevitably escape, thereby making the devices less effective for odor absorption and very ineffective for flatus noise.

Therefore, there currently exists a need for a device and associated methods to help men and women to simultaneously suppress, reduce, or eliminate the offensive noise and odor of flatus gas passing.

SUMMARY OF THE INVENTION

The present invention resolves the many shortcomings of prior devices. The present invention provides devices and methods which offers a low-cost, disposable and/or reusable way to suppress, reduce, or eliminate flatulence noise, while also simultaneously suppressing, reducing, or eliminating odor. The present invention also helps avoid soiling of undergarments by small excretions from flatulence. This invention accomplishes all of those ends simply and inexpensively without the need for the complexity of bulky pads, tight fitting undergarments, special clothing, tapes, adhesives, external devices that one must transport or sit on, or inserting a device deep into the rectum, etc.

A first aspect of the present invention provides a pad, preferably a soft, flexible, foldable pad, containing therein an odor absorbing material, such as activated charcoal and/or an activated carbon cloth filter. Preferably, the pad has at least three layers: two layers of hypo-allergenic filter cloth (for comfort and further effectiveness) and a layer of odor absorbing material sandwiched between the two layers of soft, and comfortable filter cloth. The pad, when properly used as described below, suppresses, reduces, or eliminates flatus noise and odor.

A second aspect of the present invention provides methods for reducing, suppressing, or eliminating noise and odor of flatus gas. The method includes inserting at least a portion of the pad into the anal opening or pressing at least a portion of the pad against the anus and between the buttocks to hold it in place. The excess pad not inserted in the anal opening may be tucked in place between the buttocks to further reduce, suppress, or eliminate the noise and odor of flatus gas. When positioned in or against the anal opening, the gas escaping from the anus is forced through the pad so that the gas escapes in a controlled silent and odorless manner. The pad, when placed in or against the anal opening, prevents the anal tissue, sphincter muscles, and/or buttocks from loudly reverberating, while simultaneously absorbing the odor from the escaping flatus gas. Importantly, the methods use the sphincter muscle and/or the muscles of the buttocks as a method to hold the pad in place without any need for adhesives or further complexity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. The objects and advantages of the invention will become apparent from a study of the following specification when viewed in light of the accompanying drawings, in which like elements are given the same or analogous reference numerals and wherein.

DETAILED DESCRIPTION OF THE PREFERRED EMBODIMENTS

Figure 1:
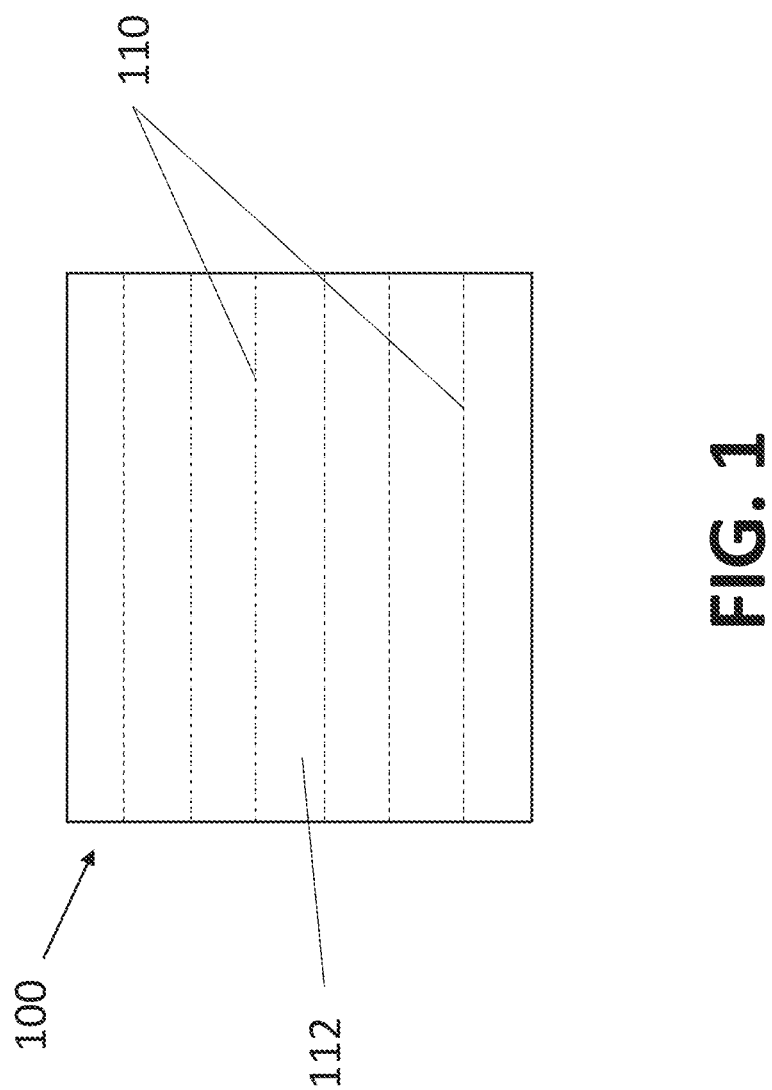
FIG. 1 is an elevational view of a pad of the present invention.

Reference will now be made in detail to exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in connection with the exemplary embodiments and methods.

This description of exemplary embodiments is intended to be read in connection with the accompanying drawings, which are to be considered part of the entire written description. In the description, relative terms such as "horizontal," "vertical," "up," "down," "upper", "lower", "right", "left", "top", "bottom", "forward", and "backward" as well as derivatives thereof (e.g., "horizontally," "downwardly," "upwardly," etc.) should be construed to refer to the orientation as then described or as shown in the drawings. These relative terms are for convenience of description and normally are not intended to require a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. Additionally, the word "a" and "an" as used in the claims means "at least one" and the word "two" as used in the claims means "at least two".

Figure 2:
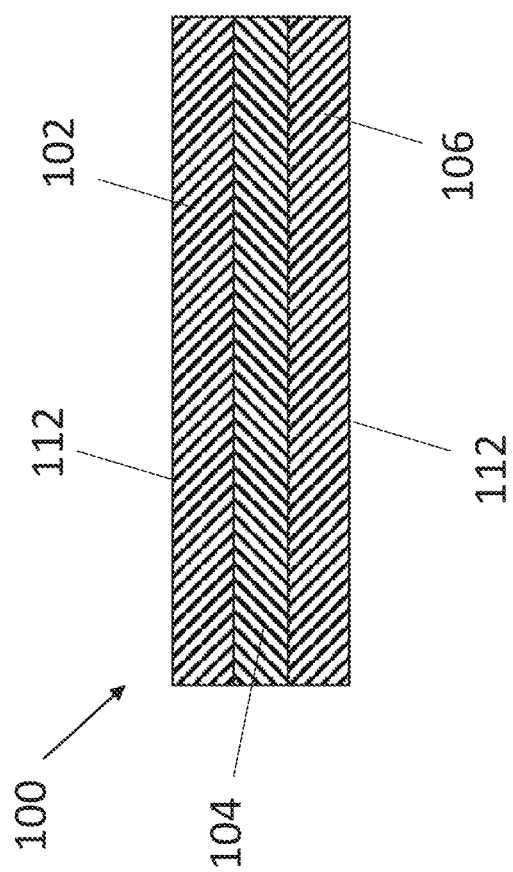
FIG. 2 is a cross-sectional view of the pad.

In an embodiment, the present invention provides a pad 100, preferably a soft, flexible, foldable pad, for suppressing, reducing, or eliminating noise and foul odor of flatus gas. Referring to FIGS. 1-2, the pad 100 includes a flat sheet containing an odor absorbing material therein. The sheet of material may be of variety of shapes, however, rectangular, square, circular, or elliptical shape is preferred. Preferably, a square pad 100 has dimensions of about 2-4 in. by about 2-4 in., more preferably about 3 in by 3 in. Pads 100 having different shapes should have dimensions to yield approximate the same area as the square pad. For example, a circular pad 100 may have a diameter of about 3-4 in. The pad 100 may also include varying densities of odor absorbing material and sound neutralizing material Although a flat sheet is preferred, the pad 100 may be formed of other shapes, such as a cylinder (similar to a tampon).

The pad 100 contains an odor absorbing material incorporated therein. The preferred odor absorbing material is, but not limited, activated charcoal fibers, activated carbon cloth, or other odor and sound absorption materials. Most preferably, the odor absorbing material is an activated carbon cloth that is commercially available, e.g., from various manufacturers throughout the world such as Calgon Carbon or Charcoal House. The activated carbon cloth is a woven or non-woven cloth material which is infused with activated charcoal. More than one layer of the activated carbon cloth may be included for additional odor absorption is desired.

Typically, about 1-3 layers of the activated carbon cloth are used. The activated carbon cloth may be used at different thicknesses to achieve the same result as using multiple layers. The odor absorbing material may also be a sponge impregnated with activated charcoal. Importantly, the pad 100 includes no adhesive or other mechanism for use and attachment to the user and is preferably made completely of soft, flexible, and foldable materials, such as cloth or foam.

In certain embodiments, the pad 100 may include a lubricant or topical ointment on its exterior surfaces 112 to provide lubrication for comfort or to help with sensitive skin and irritations. The lubricant or topical ointment may be sprayed or impregnated on to the exterior surfaces. The topical ointment may also include medication, such as, but not limited to, petroleum jelly, such as Aquaphor and Vaseline, body lotion, hemorrhoid cream/ointment, such as Preparation H, and other prescription or over-the-counter topical salves, creams, and ointments. Alternatively, the user may apply lubricant or topical ointment to the exterior surface 112 before using the pad 100.

Referring to FIG. 2, the pad 100 is preferably constructed as a three-layer structure having a center layer 104 of the odor absorbing material sandwiched between a top layer 102 and a bottom layer 106 of a porous material. The porous material of the top and bottom layers 102, 106 is a gas permeable material which may be made from polyester, polypropylene, cotton, or nylon filter cloth. Preferably, the porous material is a non-woven filter fabric. The three layers 102, 104, 106 of the pad 100 may be held together with fusion from heat (heat lamination), one or more adhesives, or by stitching.

In use, the pad 100 may be partially inserted into the anal opening to hold the pad 100 in place. Preferably, the pad 100 is inserted no-more than about 0.25 in. into the anal opening so that the pad 100 is held in place between the buttocks. Alternatively, the pad 100 may be pressed against the anus and held in place by and between the buttocks. Importantly, the pad 100 must be placed in contact with the anal opening to dampen any vibration of the anal tissue, sphincter muscles, or buttocks when the gas escapes. Furthermore, placing the pad 100 in contact with the anal opening also ensures the gas escaping the anus must go through the pad 100 for odor filtration. In one embodiment, the user inserts a center part of the pad 100 into the anal opening or pressing the center part of the pad 100 against the anal opening. The remaining part of the pad 100 (not in contact with the anal opening) is also held in place by and between the buttocks to further reduce, suppress, or eliminate the noise and odor of flatus gas. The pad may also be rolled or folded before inserting into the anal opening or pressing the pad against the anal opening.

Figure 3:
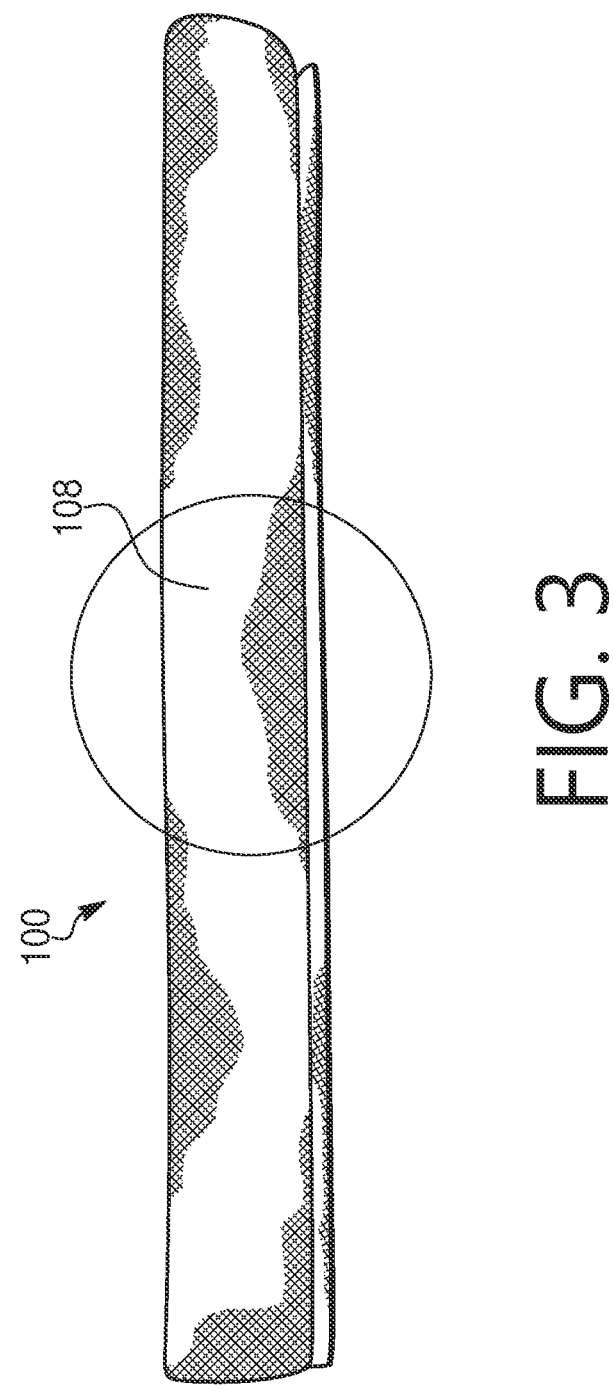
FIG. 3 is a photo showing a roll of the pad.
Figure 4:
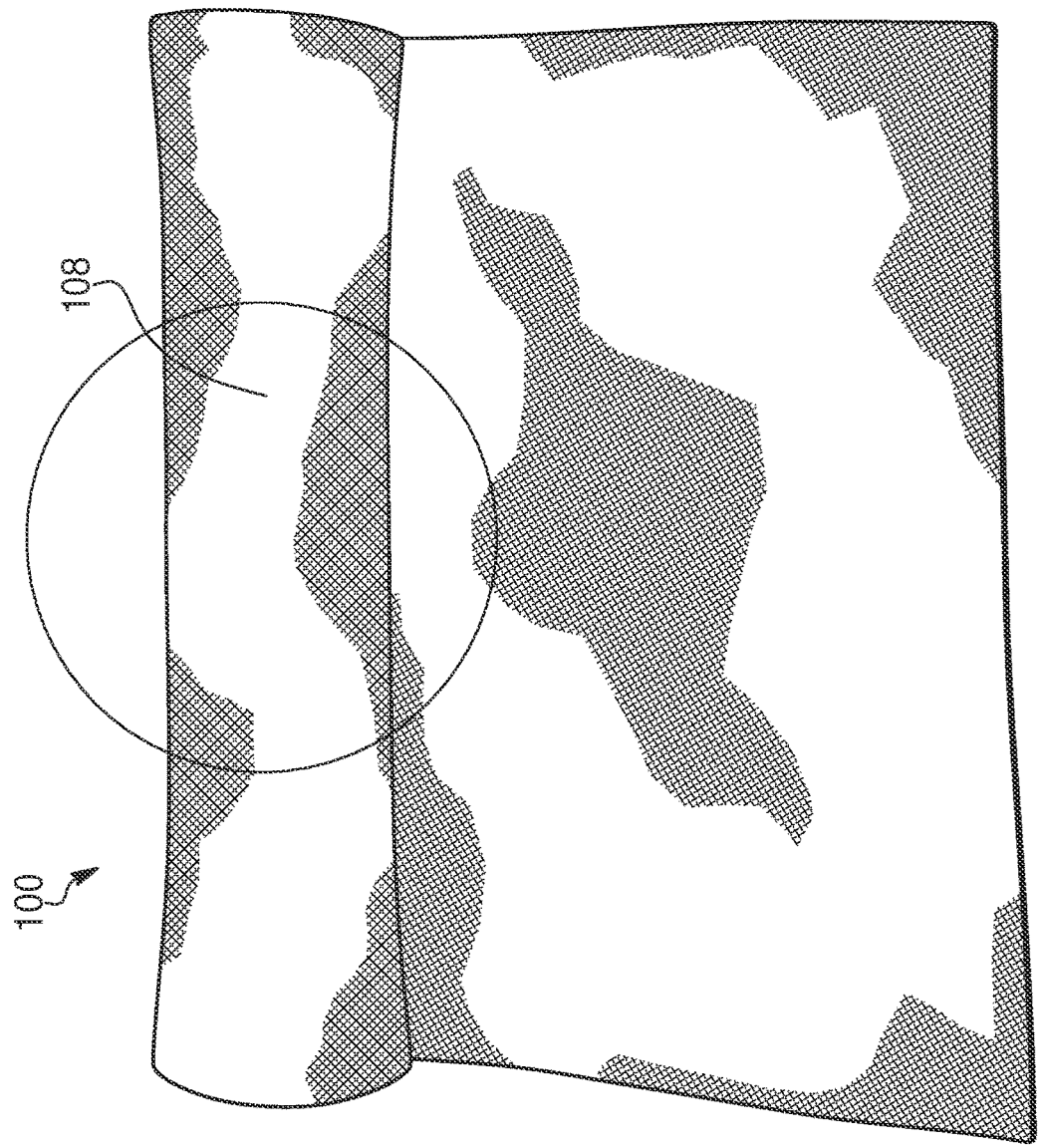
FIG. 4 is a photo showing a partial roll of the pad.

In another embodiment, the pad 100 may be rolled (FIG. 3) or partially rolled (FIG. 4) into a cylindrical shape. The middle part 108 (circled in FIGS. 3 and 4) of the roll may then be inserted into or pressed against the opening. The remaining rolled or partially rolled pad 100 (not in contact with the anal opening) is also held in place between the buttocks to further reduce, suppress, or eliminate the noise and odor of flatus gas.

Figure 5:
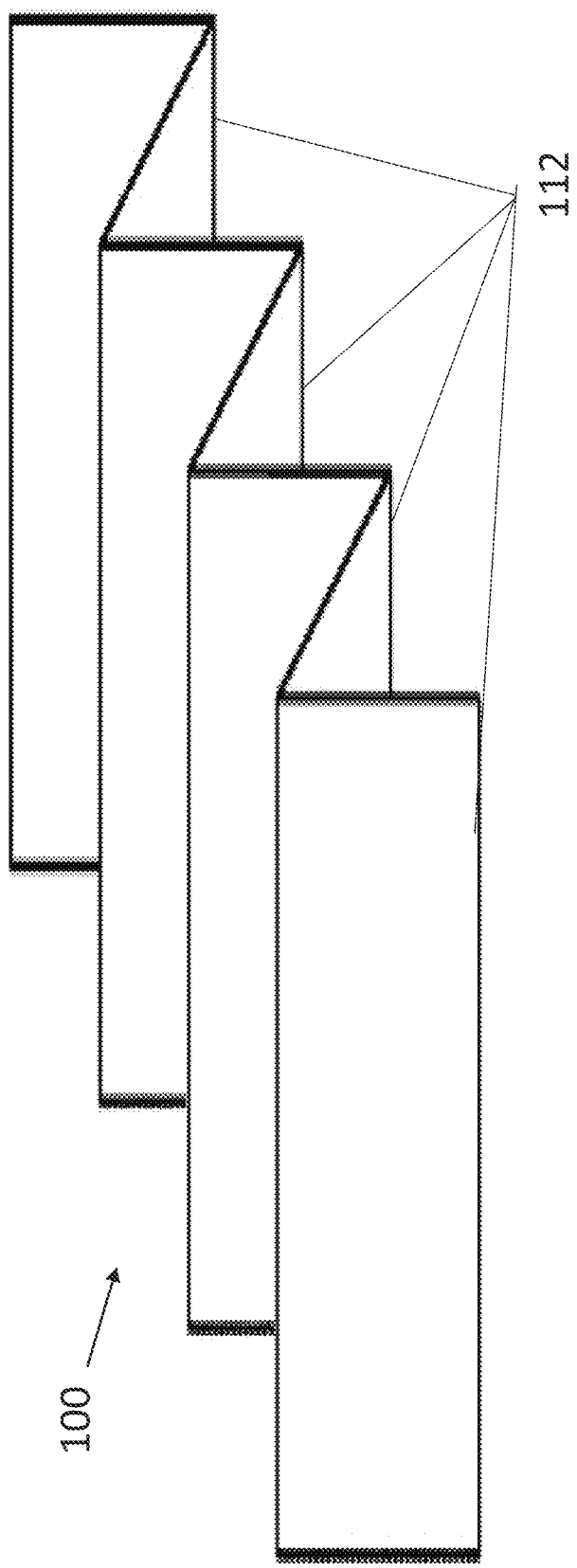
FIG. 5 is a perspective view of an accordion fold of the pad.

In yet another embodiment, the pad 100 may be accordion folded, e.g., along the dotted lines 110 shown in FIG. 1 to produce the according fold shown in FIG. 5. The accordion folded pad 100 is then compressed along the fold lines and the folded edges 112 (FIG. 5) of the folded pad 100 is then pressed together and inserted into or pressed against the anal opening. The remaining folded pad 100 (not in contact with the anal opening) is also held in place by and between the buttocks to further reduce, suppress, or eliminate the noise and odor of flatus gas. For this embodiment, the pad 100 may include guidelines thereon to assist the user in the accordion folding.

The different ways of using the pads may be combined in various combinations. For example, more than one pad 100 may be used at the same time. In an embodiment, a first pad 100 may be used by inserting or pressing a center part of the pad 100 into or against the anal opening. A second pad 100 may then be accordion folded and inserted between the buttocks and pressed against the first pad 100. This way, the first and second pads 100 provides double filtration for absorption of the flatus gas.

Although various methods have been disclosed for inserting the pad 100, the shape and size of the pad 100 placed at the anal opening can vary based on a size and shape that is comfortable and effective for the user based on their unique physical anatomy, including a protruded portion of the device that can fit around the user's finger that can be sanitarily inserted/tucked into or pressed against the anal opening leaving additional material outside of the anus tucked between the buttocks for convenience, comfort and effectiveness. Additionally, optional lubricants or topical creams/ointments may be added by the user for ease of placement, insertion, healing, comfort, or therapy. The user may add the optional lubricants or topical creams/ointments to the pad 100 or to the anal opening or buttocks.

When placed into or against the anal opening, the pad 100 suppresses, reduces, or eliminates gas passing noise by repressing uncontrolled vibration and reverberation of the anal tissue, sphincter muscles, and/or the buttocks. Additionally, the gas must pass through the pad 100, and thereby the odor absorbing material, when it exits the anus. The odor absorbing material absorbs the odor to suppress, reduce, or eliminate the noxious odor from the flatus gas. The present invention provides devices and methods for simultaneously suppressing, reducing, or eliminating flatulence noise and odor, without the need for adhesives or mechanical means to keep the device in place on the user.

Although certain presently preferred embodiments of the invention have been specifically described herein, it will be apparent to those skilled in the art to which the invention pertains those variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for suppressing, reducing, or eliminating noise and odor of flatus gas, the method comprising the steps of
    a) providing a pad comprising a sheet of material having a center layer of odor absorbing material sandwiched between a top layer and a bottom layer of porous material;
    b) rolling the pad into a cylindrical shape or accordion folding the pad;
    c) inserting a center portion of the rolled or accordion folded pad into or pressing a center portion of the rolled or accordion folded pad against an anal opening; and
    d) holding remaining portions of the rolled or accordion folded pad between the buttocks.

2. The method of claim 1, wherein the pad is rectangular, square, circular, or elliptical in shape.

3. The method of claim 1, wherein the odor absorbing material is activated charcoal or activated carbon fiber.

4. The method of claim 1, wherein the odor absorbing material is activated carbon cloth.

5. The method of claim 1, wherein the pad includes no adhesive.

6. The method of claim 1, wherein the odor absorbing material is a sponge having activated charcoal therein.

7. The method of claim 1, wherein the pad further comprising a lubricant or topical ointment on an exterior surface thereof.

8. The method of claim 1, wherein the porous material is polyester, polypropylene, cotton, or nylon cloth.

9. The method of claim 1, wherein the porous material is a non-woven filter fabric.

10. The method of claim 1, wherein the layers are held together by heat lamination, adhesive, or stitching.

11. The method of claim 1, wherein the inserting step comprises inserting the pad no more than 0.25 in. into the anal opening.

12. The method of claim 1, further comprising adding a lubricant or topical ointment before step b.

13. The method of claim 1, further comprising a step of providing a second pad comprising an odor absorbing material, accordion folding the second pad, and inserting the second pad between the buttocks and pressing the second pad against the pad.

14. A device for suppressing, reducing, or eliminating noise and odor of flatus gas, the device comprising a pad comprising an odor absorbing material therein, wherein the pad includes no adhesive, wherein the pad comprises a sheet of material having a layer of odor absorbing material sandwiched between two layers of filter material.

* * * * *